United States Patent [19]
Garvin et al.

[11] Patent Number: 5,514,590
[45] Date of Patent: *May 7, 1996

[54] **EXPRESSION SYSTEM COMPRISING DNA ENCODING THE SIGNAL PEPTIDE OF PROTEASE B FROM *STREPTOMYCES GRISEUS***

[75] Inventors: Robert T. Garvin, Toronto; Lawrence T. Malek, Brampton; Eric James, Canmore, all of Canada

[73] Assignee: Cangene Corporation, Mississauga, Canada

[*] Notice: The term of this patent subsequent to Jul. 26, 2008, has been disclaimed.

[21] Appl. No.: 203,644

[22] Filed: Mar. 1, 1994

Related U.S. Application Data

[63] Continuation of Ser. No. 66,938, May 25, 1993, abandoned, which is a continuation of Ser. No. 844,937, Mar. 4, 1992, abandoned, which is a continuation of Ser. No. 221,346, Jul. 18, 1988, abandoned, which is a continuation-in-part of Ser. No. 795,331, Nov. 6, 1985, abandoned.

[30] Foreign Application Priority Data

Jul. 21, 1987 [CA] Canada ................................. 542678

[51] Int. Cl.$^6$ ........................ C12N 15/76; C12N 15/12; C12N 15/62
[52] U.S. Cl. .................. 435/320.1; 536/23.4; 536/23.5; 536/24.1
[58] Field of Search ................................. 435/69.1, 71.2, 435/169, 172.1, 252.35, 320.1; 536/23.1, 23.4, 24.1, 24.3, 23.5

[56] References Cited

U.S. PATENT DOCUMENTS

| | | | |
|---|---|---|---|
| 4,745,056 | 5/1988 | Guterman et al. | 435/69.1 |
| 4,783,415 | 11/1988 | Hoshiko et al. | 435/320.1 |
| 5,200,327 | 4/1993 | Garvin et al. | 435/69.5 |

OTHER PUBLICATIONS

Ernst et al. "O-glycosylation and Novel Processing Events During Secretion of α–Factor/GM–CSF . . . ", *Biotechnology*, 5: 831–834 (1987).

Libby et al. "Expression and Purification of Native Human Granulocyte–Macrophage Colony Stimulating . . . ", *DNA*, 6(3): 221–229 (1987).
Vierira et al. "The pUC plasmids, an M13mp7–derived system for insertion mutagenesis and sequencing . . . ", *Gene*, 19: 259–268 (1982).
Bender et al., "Secretory Synthesis of Human Interleukin–2 by *Streptomyces lividans*," *Gene* 86:227–232 (1990).
Chang et al., "Secretion of Heterologous Proteins in *Streptomyces lividans*," Biology of Actinomycetes Okami et al. (ed.), Japan Scientific Societies Press 103–107 (1988).
Cantrell, M. A. et al. (1985) Proceeding of the National Academy of Sciences, vol. 82, pp. 6250–6254.
Lathe, R. (1985) Journal of Molecular Biology, vol. 183, pp. 1–12.
Letoffe, S. et al. (1991) J. Bacteriol, 173(7), 2160–2166.
Bibb, M. J., et al. (1985) Mol. Gen. Genet. 199, 26–36.
Henderson, G., et al. (1987) J. Bacteriol 169(8), 3778–3784.
Jurasek, L., et al. (1974) Biochem, Biophys. Res. Comm. 61(4), 1095–1100.
Duez, C., et al. (1987) Eur. J. Biochem 162, 509–518.
Bibb, M. J., et al. (1987) J. Gen. Microbiol. 133, 2089–2096.

*Primary Examiner*—Richard A. Schwartz
*Assistant Examiner*—Philip W. Carter
*Attorney, Agent, or Firm*—Foley & Lardner

[57] ABSTRACT

A DNA signal sequence initially isolated from *Streptomyces griseus* encodes a signal peptide which directs the secretion, via a fused intermediate, of a protein from the cell within which the DNA signal sequence is expressed. The signal sequence is derived from genes encoding protease A and protease B of *S. griseus*. The DNA signal sequence encodes a thirty-eight amino acid signal peptide. A DNA construct, including the DNA signal sequence and a gene sequence encoding a protein, when transformed into a living cell by a suitable vector, results in the signal peptide correctly directing the secretion of a mature protein of desired structure, particularly from prokaryotic genera selected for their ability to display enzymatic activity of a type typified by, but not exclusive to, that of protein disulphide oxidoreductase, EC 5.3.4.1, more particularly in the genera Streptomyces, and most particularly in *Streptomyces lividans* 66.

3 Claims, 12 Drawing Sheets

GTCGACCCCCATCTCATTCCGGGCTCGCGGGCGCGAATCCGGCCTTGCGTCAGGGACGGTCCCCGTCAACGATTC

CAGCGTGCAACTTGGCAGGTTCACGCCCACTCCCACTGGGTGAGAACCTCGCGCACCAACGGCCCCACCTCACCC
                   -116
              .....  M  T  F  K  R  F  S  P  L  S  S  T  S  R
GACCGGGCCGTCCCCCCATACCTCGGAGGATCTCGTGACCTTCAAGCGCTTCTCGCCGCTCAGCAGCACGTCAAG
  -100                                                       -80  ↓
 Y  A  R  L  L  A  V  A  S  G  L  V  A  A  A  A  L  A  T  P  S  A  V  A  A
ATATGCACGGCTCCTCGCCGTGGCCTCCGGCCTGGTGGCCGCCGCGGCCCTGGCCACCCCCTCGGCCGTCGCCGC
                                 -60
  P  E  A  E  S  K  A  T  V  S  Q  L  A  D  A  S  S  A  I  L  A  A  D  V  A
TCCCGAGGCGGAGTCCAAGGCCACCGTTTCGCAGCTCGCCGACGCCAGCTCCGCCATCCTCGCCGCTGATGTGGC
                           -40
   G  T  A  W  Y  T  E  A  S  T  G  K  I  V  L  T  A  D  S  T  V  S  K  A  E
GGGCACCGCCTGGTACACGGAGGCGAGCACGGGCAAGATCGTCCTCACCGCCGACAGCACCGTGTCGAAGGCCGA
                 -20
   L  A  K  V  S  N  A  L  A  G  S  K  A  K  L  T  V  K  R  A  E  G  K  F  T
ACTGGCCAAGGTCAGCAACGCGCTGGCGGGCTCCAAGGCGAAACTGACGGTCAAGCGCGCCGAGGGCAAGTTCAC
                                                                        20
  P  L  I  A  G  G  E  A  I  T  T  G  G  S  R  C  S  L  G  F  N  V  S  V  N
CCCGCTGATCGCGGGCGGCGAGGCCATCACCACCGGTGGCAGCCGCTGTTCGCTCGGCTTCAACGTGTCGGTCAA
                               40
  G  V  A  H  A  L  T  A  G  H  C  T  N  I  S  A  S  W  S  I  G  T  R  T  G
CGGCGTCGCCCACGCGCTCACCGCCGGCCACTGCACCAACATCAGCGCCAGCTGGTCCATCGGCACGCGCACCGG
                             60
  T  S  F  P  N  N  D  Y  G  I  I  R  H  S  N  P  A  A  A  D  G  R  V  Y  L
AACCAGCTTCCCGAACAACGACTACGGCATCATCCGCCACTCGAACCCGGCGGCGGCCGACGGCCGGGTCTACCT
                             80
  Y  N  G  S  Y  Q  D  I  T  T  A  G  N  A  F  V  G  Q  A  V  Q  R  S  G  S
GTACAACGGCTCCTACCAGGACATCACGACGGCGGGCAACGCCTTTGTGGGGCAGGCCGTCCAGCGCAGCGGCAG
    100                                                    120
  T  T  G  L  R  S  G  S  V  T  G  L  N  A  T  V  N  Y  G  S  S  G  I  V  Y
CACCACCGGGCTGCGCAGCGGCTCGGTCACCGGCCTCAACGCCACGGTCAACTACGGTTCCAGCGGGATCGTGTA
                                 140
  G  M  I  Q  T  N  V  C  A  E  P  G  D  S  G  G  S  L  F  A  G  S  T  A  L
CGGCATGATCCAGACCAACGTCTGTGCCGAGCCCGGTGACAGTGGAGGCTCGCTCTTCGCGGGCAGCACCGCTCT
                                 160
  G  L  T  S  G  G  S  G  N  C  R  T  G  G  T  T  F  Y  Q  P  V  T  E  A  L
GGGTCTCACCTCCGGCGGCAGTGGCAACTGCCGGACCGGCGGCACCACGTTCTACCAGCCCGTCACCGAGGCGCT
                               181                                -41.0
  S  A  Y  G  A  T  V  L  *
GAGCGCCTACGGGGCAACGGTCCTGTAGCCGGTGCCACCGGGGCTTCGGGCTGACCGCCGACCGGCCGCCCGAAG                               -30.8
CCCCGCGCGACGCCCCACCCCGGCGGACCGTGCTCGCGCGCGGTCCGCCCTCGCCGTGCCACGAACCCCACCGTC

CTTTCCCCGTCAGGCGCCTGCCGCTCGACCCGCATCGCGAAGTTGCCGAGAGTGGCCGGCTCGCACCGGCACTGC

TGAAGTCCTGCCCTCGCCCCACGGTCCGGTTCGCGCCCGCCCGGACGCGGACCCGCGCCTGGGGAAGCCCTCACT

CAACCCCGTTGCGCGCGGATGAGGTCGCGATACCAGGCGAAGGAGGCCTTCGGGGTGCGGACCTGTGTCTCGTGG

TCGAC

CGCTGTGCCCGCCGTGCGCCTTCGCCGATCACTTCATCTGCCCGTTCCCGCCCCCGGGCAACACGCTCGCCGCGG

CGGTTTTGGCGGGGGAGCGGAACCGGATCGACGCCTGACCCGCGCGAGGCCCCACCGGCCCCGGCAGCCGCACGG  -51.0

CTCCCGGGGCCGGTGACGGATGTGACCCGCGTGGCCGAAAGGCATTCTTGCGTCCCCCGTCCGGCCCCCTCGATA

CTCCGGTCAGCGATTGTCAGGGGCACGGCGAATTCGAAATCCGGACAGGCCCCCGACTGCGCCTCACGGGCCCGC
                                              -114
                                ....      M   R   I   K   R   T   S   N   R   S   N
CACCCCACAGGAGGGCCCCCGATTCCCCTCGGAGGAACCCGAAGTGAGGATCAAGCGCACCAGCAACCGCTCGAA
    -100                                                                -80
  A   A   R   R   V   R   T   T   A   V   L   A   G   L   A   A   V   A   A   L   A   V   P   T   A
CGCGGCGAGACGCGTCCGCACCACCGCCGTACTCGCGGGGCTCGCCGCCGTCGCGGCGCTGGCCGTTCCCACCGC
            ↓                                               -60
  N   A   E   T   P   R   T   F   S   A   N   Q   L   T   A   A   S   D   A   V   L   G   A   D   I
GAACGCCGAAACCCCCCGGACGTTCAGTGCCAACCAGCTGACCGCGGCGAGCGACGCCGTGCTCGGCGCCGACAT
                                                    -40
  A   G   T   A   W   N   I   D   P   Q   S   K   R   L   V   V   T   V   D   S   T   V   S   K   A
CGCGGGCACCGCCTGGAACATCGACCCGCAGTCCAAGCGCCTCGTCGTCACCGTCGACAGCACGGTCTCGAAGGC
                        -20
  E   I   N   Q   I   K   K   S   A   G   A   N   A   D   A   L   R   I   E   R   T   P   G   K   F
GGAGATCAACCAGATCAAGAAGTCGGCGGGCGCCAACGCCGACGCGCTGCGGATCGAGCGCACCCCCGGGAAGTT
            ↓                                                           20
  T   K   L   I   S   G   G   D   A   I   Y   S   S   T   G   R   C   S   L   G   F   N   V   R   S
CACCAAGCTGATCTCCGGCGGCGACGCGATCTACTCCAGCACCGGACGCTGCTCGCTCGGCTTCAACGTCCGCAG
                                                    40
  G   S   T   Y   Y   F   L   T   A   G   H   C   T   D   G   A   T   T   W   W   A   N   S   A   R
CGGCAGCACCTACTACTTCCTGACCGCCGGCCACTGCACGGACGGCGCGACCACCTGGTGGGCGAACTCGGCCCG
                                60
  T   T   V   L   G   T   T   S   G   S   S   F   P   N   N   D   Y   G   I   V   R   Y   T   N   T
CACCACGGTGCTCGGCACGACCTCCGGGTCGAGCTTCCCGAACAACGACTACGGCATCGTGCGCTACACCAACAC
                80
  T   I   P   K   D   G   T   V   G   G   Q   D   I   T   S   A   A   N   A   T   V   G   M   A   V
CACCATTCCCAAGGACGGCACGGTCGGCGGCCAGGACATCACCAGCGCCGCCAACGCCACCGTCGGCATGGCGGT
    100                                                                     120
  T   R   R   G   S   T   T   G   T   H   S   G   S   V   T   A   L   N   A   T   V   N   Y   G   G
CACCCGCCGCGGCTCCACCACCGGCACCCACAGCGGTTCGGTCACCGCACTCAACGCCACCGTCAACTACGGGGG
                                                            140
  G   D   V   V   Y   G   M   I   R   T   N   V   C   A   E   P   G   D   S   G   G   P   L   Y   S
CGGCGACGTCGTCTACGGCATGATCCGCACCAACGTGTGCGCGGAGCCCGGCGACTCCGGCGGCCCGCTCTACTC
                                        160
  G   T   R   A   I   G   L   T   S   G   G   S   G   N   C   S   S   G   G   T   T   F   F   Q   P
CGGCACCCGGGCGATCGGTCTGACCTCCGGCGGCAGCGGCAACTGCTCCTCCGGCGGCACGACCTTCTTCCAGCC
                                                185
  V   T   E   A   L   S   A   Y   G   V   S   V   Y   *
GGTCACCGAGGCGCTGAGCGCGTACGGCGTCAGCGTGTACTGACCGGCCCCGCCCCGGTCGGGTACGGAGCAGTC

-40.8
CGTACAAACGTGCCCCCGTCCGGAATTCCGGACGGGGGCTCCCGCTCGCCGGGGAGCTCTTGAGAGGATGTCGCC

ACGACGGGTCGCCGCTGCGCGTC

```
                                                        -60
           N A E T P R T F S A N Q L T A A S D A V L G A D I
           GAACGCGAAACCCCCGGACGTTCAGTGCCAACCAGCTGACCGCGGGAGCGACGCCGTGCTCGGCGCCGACAT
                                  -40
           A G T A W N I D P Q S K R L V V T Y D S T V S K A
           CGCGGGCACCGCTGGAACATCGACCCGCAGTCCAAGCGCCTCGTCGTCACCGTCGACAGCACGGTCTCGAAGGC
                          -20
           E I N Q I K K S A G A N A D A L R I E R T P G K F
           GGAGATCAACCAGATCAAGAAGTCGGCGGGCGCCAACGCCGACGCGCTGCGGATCGAGCGCACCCCGGGAAGTT
                                                                    20
           T K L I S G G D A I Y S S I G R C S L Q F M V R S
           CACCAAGCTCATCTCCGGCGGCGACGCGATCTACTCCAGCATCGGACGCTGCTCGCTCCAGTTCATGGTGCGCT
```

FIG.5C.

```
                    1                                                    20
         T  L  I  S  G  G  D  A  I  Y  S  S  T  G  R  C  S  L  G  F  N  V  R  S
CACCARGCTGATCTCCGGCGGCGACGCGATCTACTCCAGCACCGGACGCTGCTCGCTCGGCTTCAACGTCCGCAG
                                         40
         G  S  T  Y  Y  F  L  T  A  G  H  C  T  D  G  A  T  T  W  W  A  N  S  A  R
CGGCAGCACCTACTACTTCCTGACCGCCGGCCACTGCACGGACGGCGCGACCACCTGGTGGGCGAACTCGGCCCG
                                         60
         T  T  V  L  G  T  T  S  G  S  S  F  P  N  N  D  Y  G  I  V  R  Y  T  N  T
CACCACGGTGCTCGGCACGACCTCCGGGTCGAGCTTCCCGAACAACGACTACGGCATCGTGCGCTACACCAACAC
                                         80
         T  I  P  K  D  G  T  V  G  G  Q  D  I  T  S  A  A  N  A  T  V  G  M  A  V
CACCATTCCCAAGGACGGCACGGTCGGCGGCCAGGACATCACCAGCGCCGCCAACGCCACCGTCGGCATGGCGGT
         100                                                             120
         T  R  R  G  S  T  T  G  T  H  S  G  S  V  T  A  L  N  A  T  V  N  Y  G  G
CACCCGCCGCGGCTCCACCACCGGCACCCACAGCGGTTCGGTCACCGCACTCAACGCCACCGTCAACTACGGGGG
                                         140
         G  D  V  V  Y  G  M  I  R  T  N  V  C  A  E  P  G  D  S  G  G  P  L  Y  S
CGGCGACGTCGTCTACGGCATGATCCGCACCAACGTGTGCGCGGAGCCCGGCGACTCCGGCGGCCCGCTCTACTC
                                         160
         G  T  R  A  I  G  L  T  S  G  G  S  G  N  C  S  S  G  G  T  T  F  F  Q  P
CGGCACCCGGGCGATCGGTCTGACCTCCGGCGGCAGCGGCAACTGCTCCTCCGGCGGCACGACCTTCTTCCAGCC
                                         185
         V  T  E  A  L  S  A  Y  G  V  S  V  Y  *
GGTCACCGAGGCGCTGAGCGCGTACGGCGTCAGCGTGTAC
```

```
sprA   MTFKRFSPLSSTSRYARLLAVASGLVAAAALATPSAVA
       M  KR S    S    R  R   AV  GL A AALA P A A
sprB   MRIKRTSNRSNAARRVRTTAVLAGLAAVAALAVPTANA
```

```
sprA   APEAESKATVSQLADASSAILAADVAGTAWYTEASTGKI
              A   QL  AS A L AD AGTAW
sprB   ETPRTFSAN--QLTAASDAVLGADIAGTAWNIDPQSKRL sprA   VLTADSTVSKAELAKVSNALAGSKAK-LTVKRAEGKFTPL
       V T DSTVSKAE         AG  A L  R  GKFT L
sprB   VVTVDSTVSKAEINQIKKS-AGANADALRIERTPGKFTKL
```

```
sprA   IAGGEAITTGGSRCSLGFNVSVNGVAHALTAGHCTNIS
       I GG AI      RCSLGFNV        LTAGHCT
sprB   ISGGDAIYSSTGRCSLGFNVRSGSTYYFLTAGHCTDGA sprA   ASWS--------IGTRTGTSFPNNDYGIIRHSNPAAA-
       W             GT  G SFPNNDYGI R  N
sprB   TTWWANSARTTVLGTTSGSSFPNNDYGIVRYTNTTIPK sprA   DGRVYLYNGSYQDITTAGNAFVGQAVQRSGSTTGLRSG
       DG V    G  QDIT A NA VG AV R GSTTG  SG
sprB   DGTV----GG-QDITSAANATVGMAVTRRGSTTGTHSG sprA   SVTGLNATVNYGSSGIVYGMIQTNVCAEPGDSGGSLFA
       SVT LNATVNYG   VYGMI TNVCAEPGDSGG L
sprB   SVTALNATVNYGGGDVVYGMIRTNVCAEPGDSGGPLYS sprA   GSTALGLTSGGSGNCRTGGTTFYQPVTEALSAYGATVL
       G  A GLTSGGSGNC  GGTTF QPVTEALSAYG  V
sprB   GTRAIGLTSGGSGNCSSGGTTFFQPVTEALSAYGVSVY
```

EXPRESSION SYSTEM COMPRISING DNA ENCODING THE SIGNAL PEPTIDE OF PROTEASE B FROM *STREPTOMYCES GRISEUS*

This application is a continuation of application Ser. No. 08/066,938, filed May 25, 1993, abandoned, which was a continuation of Ser. No. 07/844,937, filed on Mar. 4, 1992, now abandoned, which was a continuation of Ser. No. 07/221,346, filed Jul. 18, 1988, abandoned, which was a continuation-in-part of Ser. No. 06/795,331 filed Nov. 6, 1985, abandoned.

FIELD OF THE INVENTION

This invention relates to a biologically pure DNA signal sequence which encodes an amino acid signal peptide necessary for directing the secretion from certain defined hosts of proteins in bioactive form.

BACKGROUND OF THE INVENTION

Figure 1:
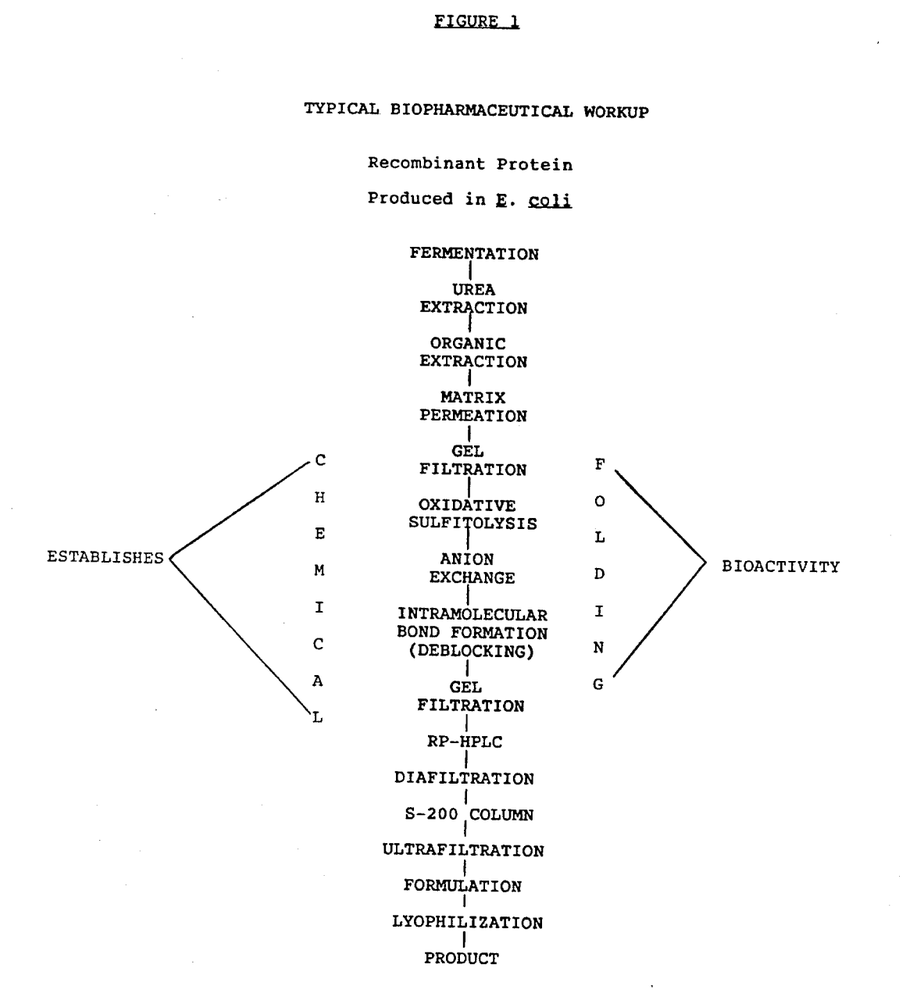
FIG. 1 illustrates downstream processing.

In the biological production of commercially viable proteins by the fermentation of microorganisms, the ability to produce the desired proteins by fermentation with secretion of the proteins by the microorganisms into the broth is very significant. However, there are many commercially viable proteins encoded by genetically engineered DNA constructs which are not secreted by the cells in which the DNA is expressed. This often necessitates harvesting the cells, bursting the cell walls, recovering the desired proteins in pure form and then chemically re-naturing the pure material to restore its bioactive function. This downstream processing, as it is called, is illustrated in FIG. 1.

Some cells and microorganisms carry out the biological equivalent of downstream processing by secreting proteins in bioactive form. The mechanism which directs the secretion of some proteins through the cell walls is not fully understood. For example, in *Streptomyces griseus,* an organism used for the commercial production of Pronase, the species secretes many extra cellular proteins (Jurasek, L., P. Johnson, R. W. Olafson, and L. B. Smillie (1971), *An improved fractionation system for pronase on CM-Sephadex* Can. J. Biochem., 49:1195–1201). Protease A and protease B, two of the serine proteases secreted by *S. griseus,* have sequences which are 61% homologous on the basis of amino acid identity (Fujinaga. M., L. T. J. Delbaere, G. D. Brayer, and M. N. G. James (1985), *Refined structure of α-lytic protease at 1.7A resolution; Analysis of hyrodgen bonding and solvent structure,* J. Mol. Biol., 183:479–502; Jurasek L., M. R. Carpenter, L. B. Smillie, A. Gertler, S. Levy, and L. H. Ericsson (1974), *Amino acid sequencing of Streptomyces griseus protease B, A major component of pronase,* Biochem. Biophys. Res. Comm., 61:1095–1100; Young, C. L., W. C. Barker, C. M. Tomaselli, and M. O. Dayhoff (1978), *Serine proteases,* In M. O. Dayhoff (ed.), *Atlas of Protein Sequence and Structure* 5, suppl. 3:73–93). These proteases also have similar tertiary structure, as determined by X-ray crystallography (Delbaere, L. T. J., W. L. B. Hutcheon, M. N. G. James, and W. E. Thiessen (1975), *Tertiary structural differences between microbial serine proteases and pancreatic serine enzymes,* Nature 257:758–763; Fujinaga. M., L. T. J. Delbaere, G. D. Brayer, and M. N. G. James (1985), *Refined structure of α-lytic protease at 1.7A resolution; Analysis of hyrodgen bonding and solvent structure,* J. Mol. Biol., 183:479–502; James, M. N. G., A. R. Sielecki, G. D. Brayer, L. T. J. Delbaere, and C.-A. Bauer (1980), *Structures of product and inhibitor complexes of Streptomyces griseus protease A at 1.8. A resolution,* J. Mol. Biol., 144:43–88). Although the structures of proteases A and B have been extensively studied, the genes encoding these proteases have not been characterized before.

SUMMARY OF THE INVENTION

In accordance with this invention, the genes encoding protease A and protease B of *S. griseus* have been isolated and investigated to reveal DNA sequences which each direct the secretion of an encoded protein fused either directly or indirectly to a signal peptide encoded by the DNA.

According to an aspect of the invention, a recombinant DNA sequence comprises a signal sequence and a gene sequence encoding a protein. The recombinant DNA sequence, when expressed in a living cell, encodes an amino acid signal peptide with the protein. The signal peptide directs secretion of the protein from a cell within which the DNA signal sequence is expressed.

According to another aspect of the invention, a biologically pure isolated DNA signal sequence encodes a 38 amino acid signal peptide which directs secretion of a recombinant gene-sourced protein linked to such 38 amino acid signal peptide, from a cell in which the DNA signal sequence is expressed. The DNA signal sequence is isolated from *Streptomyces griseus.*

According to another aspect of the invention, the DNA signal sequence in conjunction with a gene sequence encoding a protein is inserted into a vector, such as a plasmid or a phage.

According to another aspect of the invention, the DNA signal sequence is adapted for expression in a living cell having enzymes catalyzing the formation of disulphide bonds.

Figure 4A:
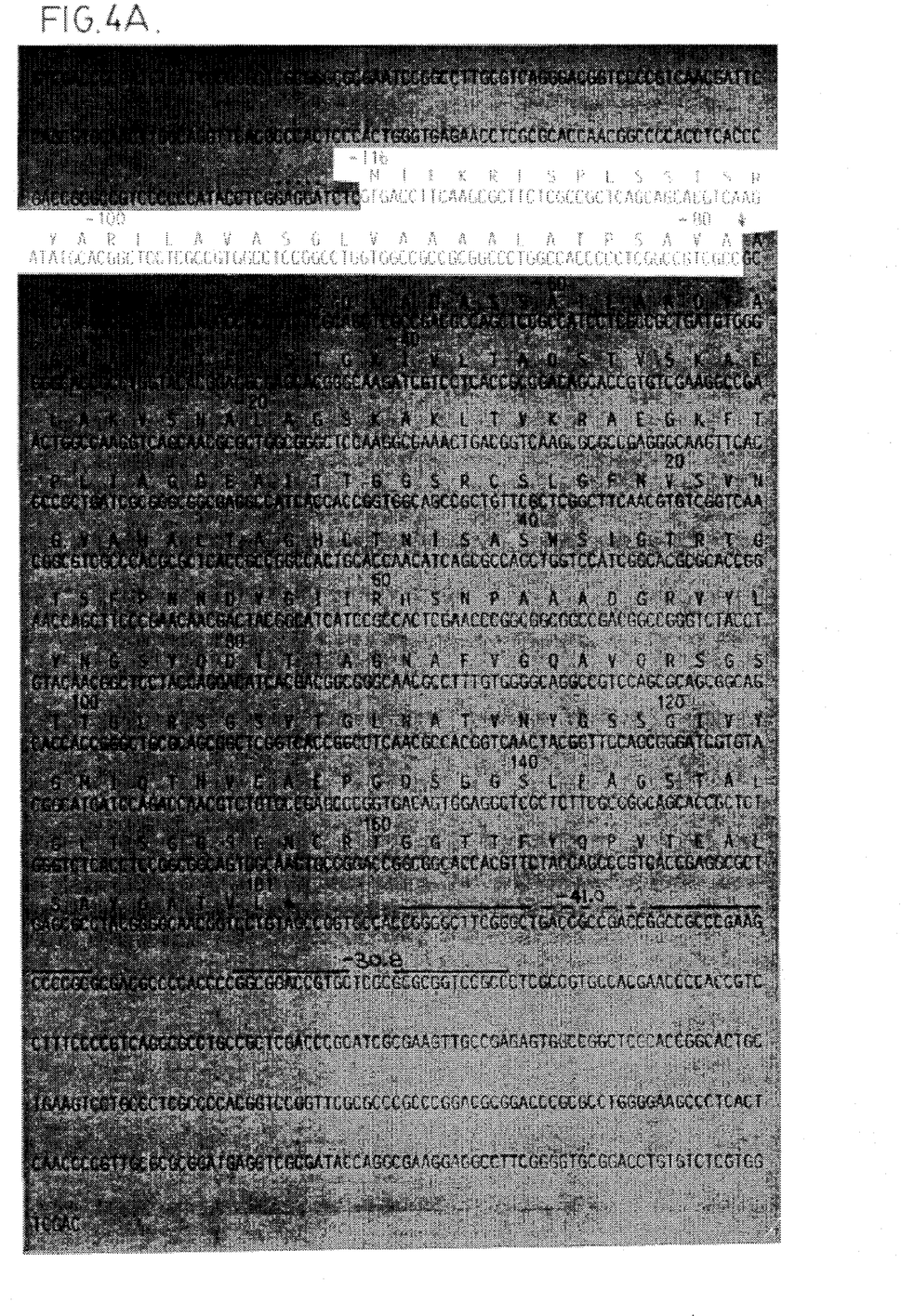
FIG. 4a is the DNA sequence encoding the sprA (protease A) signal peptide.

According to another aspect of the invention, the biologically pure isolated DNA signal sequence of FIG. 4a.

Figure 5A:
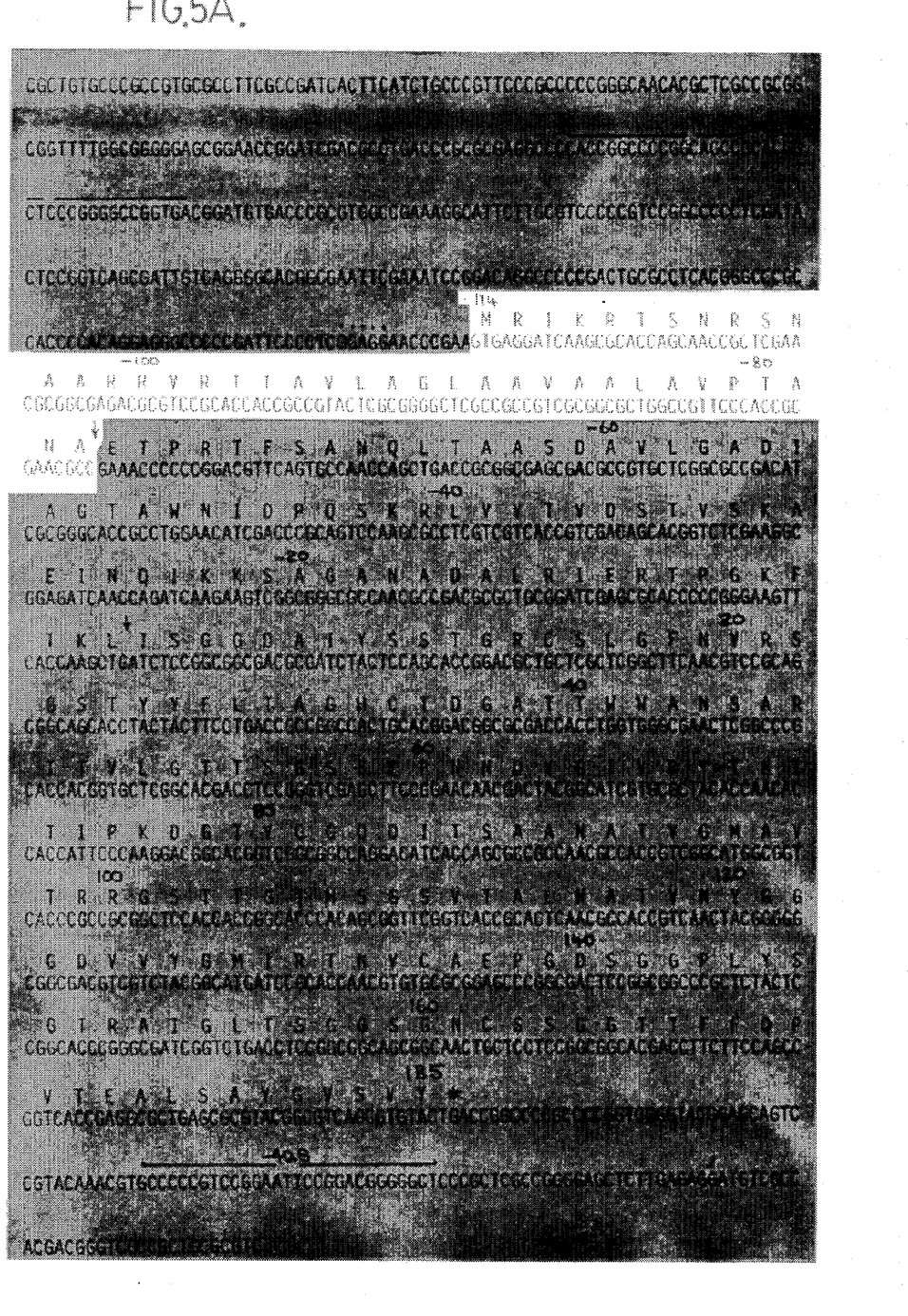
FIG. 5a is the DNA sequence encoding the sprB (protease B) signal peptide.

According to another aspect of the invention, the biologically pure isolated DNA signal sequence of FIG. 5a.

According to another aspect of the invention, a fused protein is encoded by the recombinant DNA sequence of FIG. 4 or FIG. 5.

According to another aspect of the invention, a transformed prokaryotic cell is provided which has inserted therein a suitable vector including the recombinant DNA encoding the signal protein. The transformed prokaryotic cell may be selected from the Streptomyces genera.

According to another aspect of the invention, a biologically pure culture has a transformed prokaryotic cell with the recombinant DNA sequence in a suitable vector. The culture is capable of producing, as an intermediate, the fused protein of the amino acid signal peptide and the protein. The protein itself is produced in a recoverable quantity upon fermentation of the transformed cell in an aqueous nutrient medium. The signal peptide directs secretion of the protein from the cell.

According to another aspect of the invention, a biologically pure culture, transformed with the functional signal sequence as described above, is able to direct the secretion from the cell of proteins whose bioactivity is dependent upon the formation of correctly positioned intramolecular disulphide bonds.

Figure 4B:
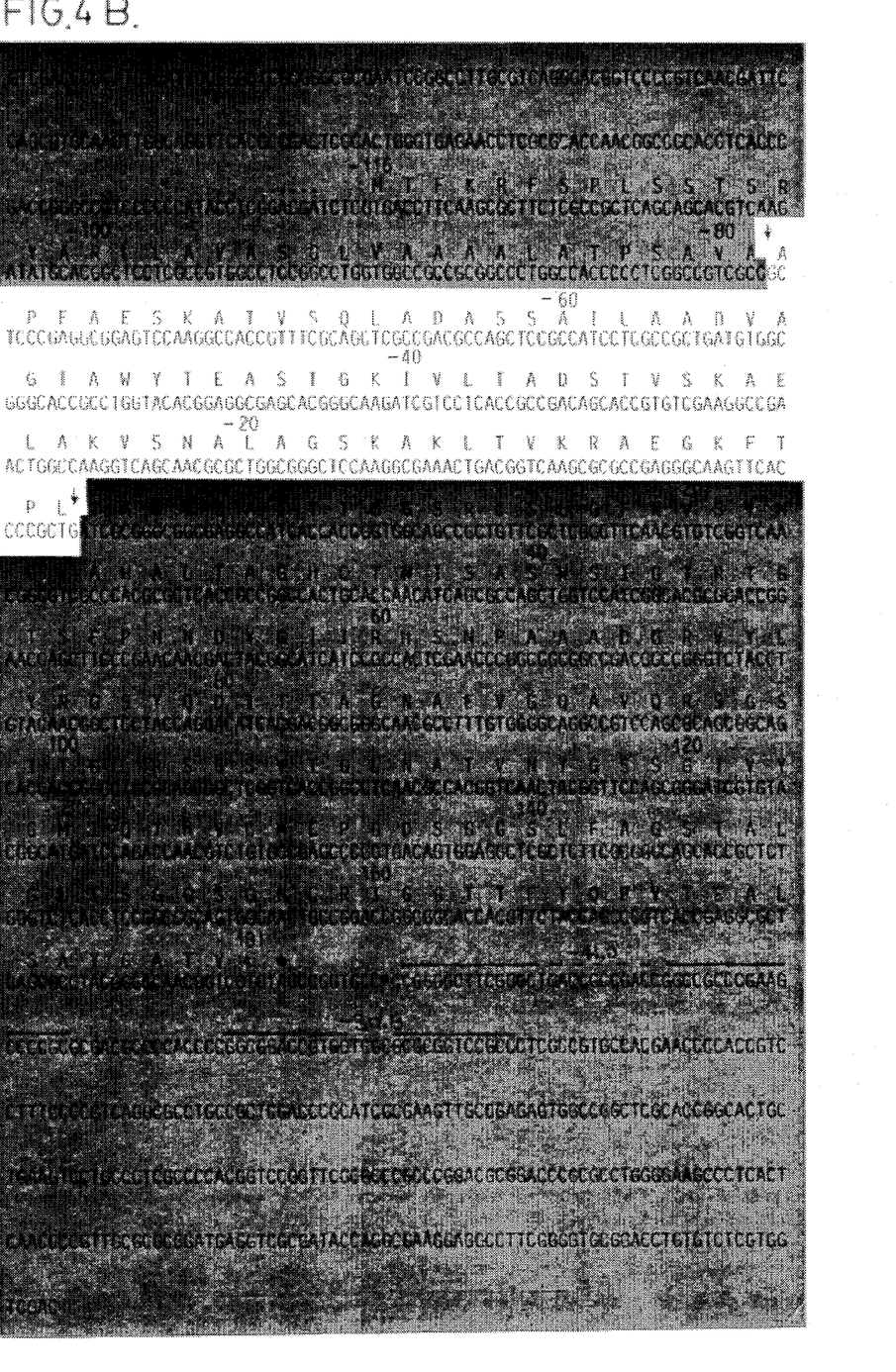
FIG. 4b is the DNA sequence encoding the sprA (protease A) propeptide.
Figure 4C:
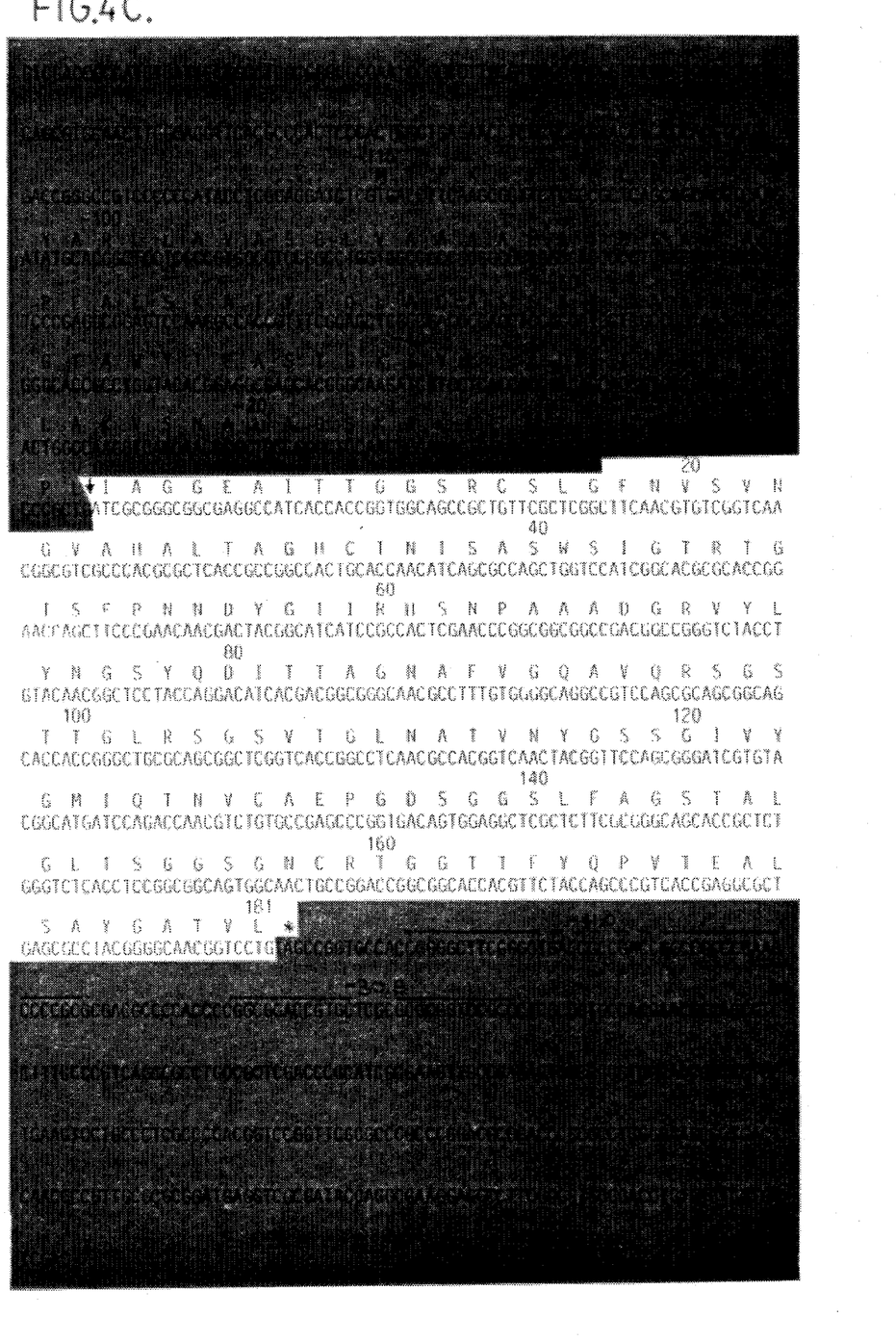
FIG. 4c is the DNA sequence encoding mature protease A.

A biologically pure DNA sequence encoding a fused protein including protease A has the combined DNA sequence of FIGS. 4a, 4b and 4c.

Figure 5B:
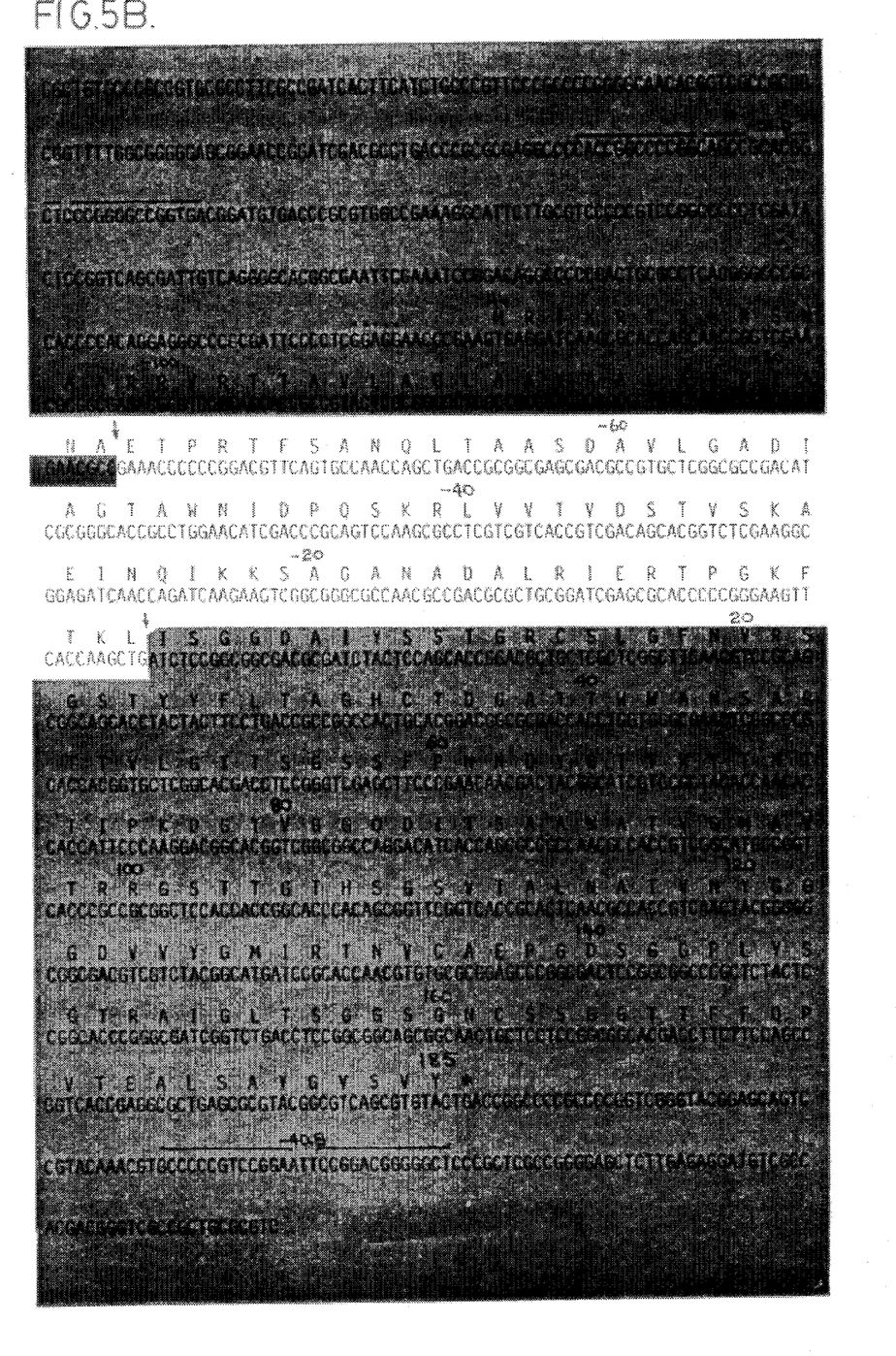
FIG. 5b is the DNA sequence encoding the sprB (protease B) propeptide.
Figure 5C:
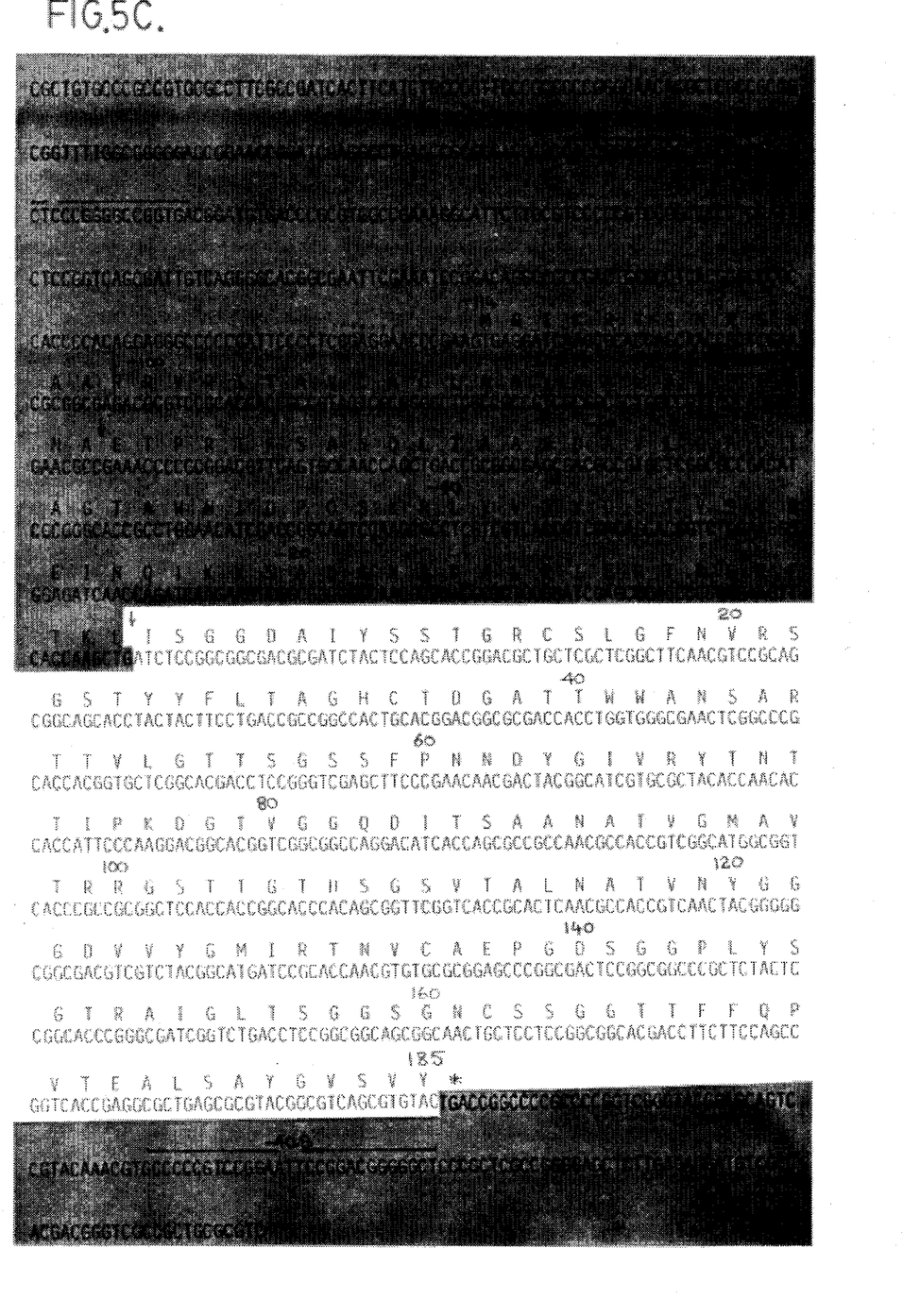
FIG. 5c is the DNA sequence encoding mature protease B.

A biologically pure DNA sequence encoding a fused protein including protease B has the combined DNA sequence of FIGS. 5a, 5b and 5c.

BRIEF DESCRIPTION OF THE DRAWINGS

With reference to the figures, a variety of short forms have been used to identify restriction endonucleases, amino acids, deoxyrbonucleic acids and related information. Standard nomenclature has been used in identifying all of these components as are readily appreciated by those skilled in the art.

Preferred embodiments of the invention are described with respect to the drawings, wherein:

FIG. 4 is the DNA sequence of sprA;

FIG. 5 is the DNA sequence of sprB;

DETAILED DESCRIPTION OF THE PREFERRED EMBODIMENTS

The organism *Streptomyces griseus* is a well recognized microorganism. It is commercially used for the production of the enzyme Pronase. It is appreciated, however, that this organism also secretes two enzymes, protease A and protease B, which are both serine proteases. Although the structure of proteases A and B have been extensively studied, the genes encoding these proteins, and the manner in which this genetic information is used to signal secretion by the cells, is not understood. According to this invention, the genes which encode protease A and protease B and provide for the secretion of these proteins in bioactive form have been discovered. It has been determined that each of protease A and B is included in a precursor protein which is processed to remove an amino-terminal polypeptide portion from the mature protease. It has further been determined that each of protease A and B precursor proteins is enzymatically processed to form correctly-positioned intramolecular disulphide bonds, which processing is concomitant with removal of the amino terminal addressing peptide from the mature precursor. The discovered genes, which encode proteases A and B, their intermediate address-competent forms, and their control elements, have been designated sprA and sprB.

As discussed in the following articles, Jurasek, L., M. R. Carpenter, L. B. Smillie, A. Gertler, S. Levy, and L. H. Ericsson (1974), *Amino acid sequencing of Streptomyces griseus protease B, a major component of pronase.*, Biochem. Biophys. Res. Comm. 61:1095–1100; Young, C. L., W. C. Barker, C. M. Tomaselli, and M. O. Dayhoff (1978), *Serine proteases,* In M. O. Dayhoff (ed.), *Atlas of Protein Sequence and Structure* 5, suppl. 3:73–93, proteases A and B are homologous proteins containing several segments of identical amino acid sequence. In accordance with this invention, the genetic code, which makes and directs the secretion of each of proteases A and B, has identical DNA sequences corresponding to the regions of identicality for the homologous proteins proteases A and B. In order to isolate the genes, this assumption, that identicality in portions of the gene sequences would occur, was made so that an oligonucleotide probe could be designed from one of the similar regions in the sequences.

In order to extrapolate the gene sequence which would encode the similar amino acid sequence, the known codon bias for Streptomyces was relied upon to develop the nucleotide probe (see Bernan, V., D. Filpula, W. Herber, M. Bibb, and E. Katz (1985), *The nucleotide sequence of the tyrosinase gene from Streptomyces antibiotics and characterization of the gene product,* Gene 37:101–110; Bibb, M. J., M. J. Bibb, J. M. Ward, S. N. Cohen (1985), *Nucleotide sequences encoding and promoting expression of three antibiotic resistance genes indigenous to Streptomyces.,* Mol. Gen. Genet. 199:26–36; (Thompson, C. J., and G. S. Gray (1983), *Nucleotide sequence of a streptomycete aminoglycoside phosphotransferase gene and its relationship to phosphotransferases encoded by resistance plasmids,* Proc. Natl. Acad. Sci. USA 80:5190–5194). Once the probe was constructed, it was then possible to probe the DNA sequences of *S. griseus* to determine if there were any corresponding nucleic acid sequences in the microorganism. Since it was known that there were two proteases, A and B, the oligonucleotide probe should have revealed two DNA fragments detected by hybridization analysis, and in fact, not only did the probe hybridize equally to two fragments generated in the genomic library of *S. griseus,* but also two fragments generated by BamHI digest (8.4 kb and 6.8 kb) or BglII (11 kb and 2.8 kb) were isolated from the genomic library. As a cross-check with respect to the predictability of such probe, the same fragments were detected in genomic DNA libraries of other isolates of *S. griseus.* It was noted, however, that there was no such hybridization of the oligonucleotide probe with DNA from other Streptomyces such as *S. lividans.*

Plasmids were constructed containing digested fragments of *S. griseus.* The oligonucleotide probe was used to isolate developed plasmids containing sprA and sprB. The screening by use of the probe was accomplished by colony blot hybridization where approximately 15,000 *E. coli* transformants containing the developed plasmids were screened. Twelve transformants were detected by the probe and isolated for further characterization. These colonies contained two distinct classes of plasmid based on restriction analysis. As determined from the hybridization of genomic DNA, the plasmids contained either the 6.8 kb or the 8.4 kb BamHI fragment. These fragments contained the sprA and sprB genes.

The fragments as isolated by hybridization screening were tested for the expression of proteolytic activity. With these plasmids identified, such characterization may be accomplished in accordance with a variety of known techniques in accordance with a preferred embodiment of this invention.

The 6.8 kb and 8.4 kb BamHI fragments were ligated into the BglII site of the vector pIJ702. Transformants of *S. lividans* containing these constructions were tested on a milk plate for secretion of proteases. A clear zone, which represented the degradation of the milk proteins, surrounded each transformant that contained either BamHI fragment. It was noted that the clear zones were not found around *S. lividans* colonies which contained either pIJ702 only or no plasmid construct.

Proteolytic activity was also observed when the BamHI fragments were cloned in either orientation with respect to the vector, thereby minimizing the possibility of read-through transcription of an incomplete protease gene. This observation provides evidence that the two BamHI fragments contain an intact protease gene which is capable of effecting secretion in a different Streptomyces species, as for example the *S. lividans*. With this particularly relevant characterization of the BamHI fragment, and knowing that the desired gene was in these fragments, it was possible to isolate and to sequence the genes encoding protease A and protease B.

According to a preferred aspect of this invention, the particular protease gene contained within each cloned BamHI fragment was determined by dideoxy sequencing of the plasmids using the oligonucleotide probe as a primer in such analysis. The 8.4 kb BamHI fragment was found to contain SprB, because a polypeptide deduced from the DNA sequence matched a unique segment of the known amino acid sequence of protease B. The 6.8 kb BamHI fragment contained the SprA by process of elimination. The protease genes in these fragments were localized by digesting the plasmids and determining which of the restriction fragments of the plasmids were capable of hybridizing to the oligonucleotide probe.

Figure 2:
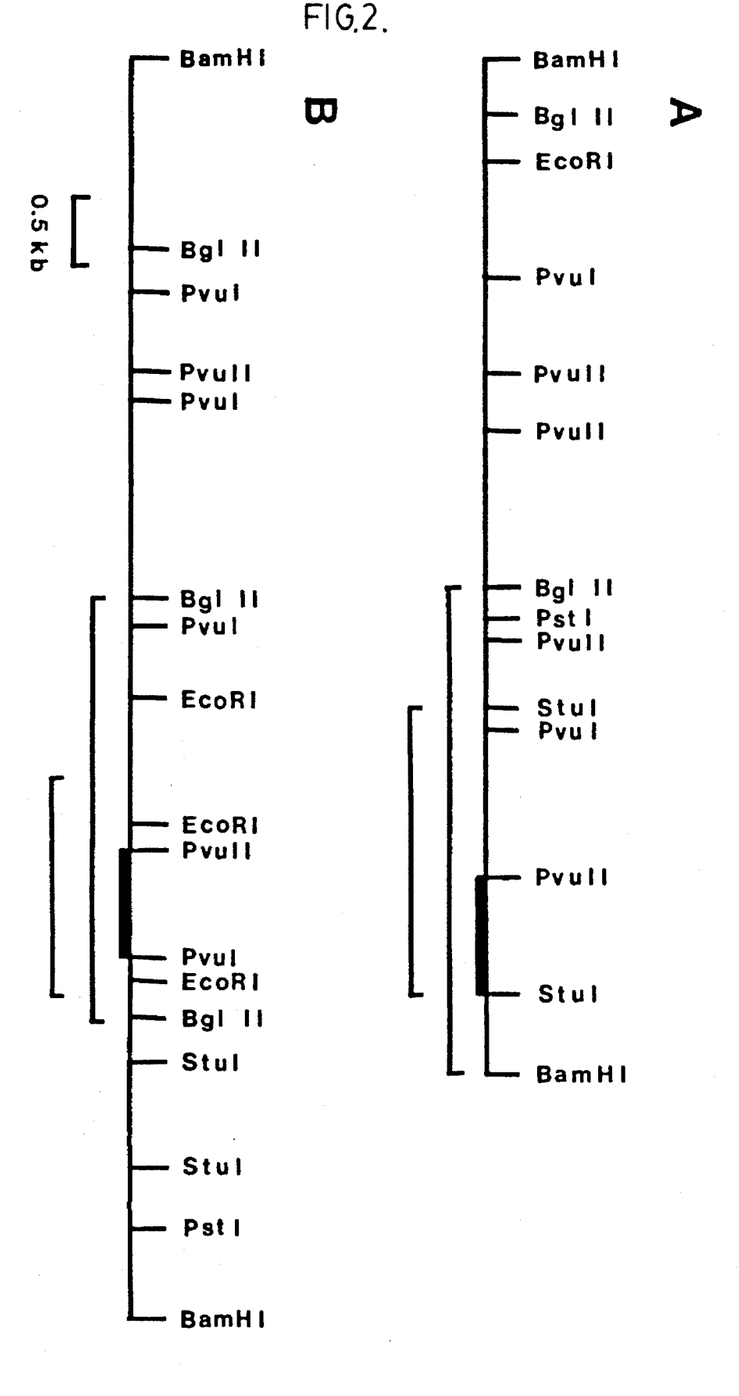
FIG. 2 shows restriction endonuclease maps of DNA fragments of sprA and sprB.

FIG. 2 shows detailed restriction maps of the 6.8 kb and 8.4 kb BamHI fragments. Hybridization to the oligonucleotide probe was confined to a 0.9 kb PvuII–StuI fragment of sprA and a 0.6 kb PvuII–PvuI fragment of sprB. Such hybridization is indicated by the heavy lines in FIG. 2. Hybridization to the cloned BamHI fragments and the 2.8 kb BglII fragment of sprB agrees with the hybridization to BamHI and BglII fragments of genomic DNA. Thus, rearrangment of the BamHI fragments containing the protease genes is unlikely to have occurred.

The functional portions of the sprA- and sprB-containing DNA were determined by subcloning restriction fragments thereof into pIJ702. The constructed plasmids were transformed into *S. lividans* and tested for proteolytic activity. The 3.2 kb BamHI–BglII fragment of sprA and the 2.8 kb BglII fragment of sprB, when subcloned into pIJ702 in either orientation, resulted in the secretion of protease from *S. lividans*. The intact protease genes were further delimited to a 1.9 kb StuI fragment for sprA and a 1.4 kb BssHII fragment for sprB. With reference to FIG. 2, each of these functionally active subclones are indicated below the restriction maps which contain the region for each gene which hybridized to the oligonucleotide probe.

Figure 3:
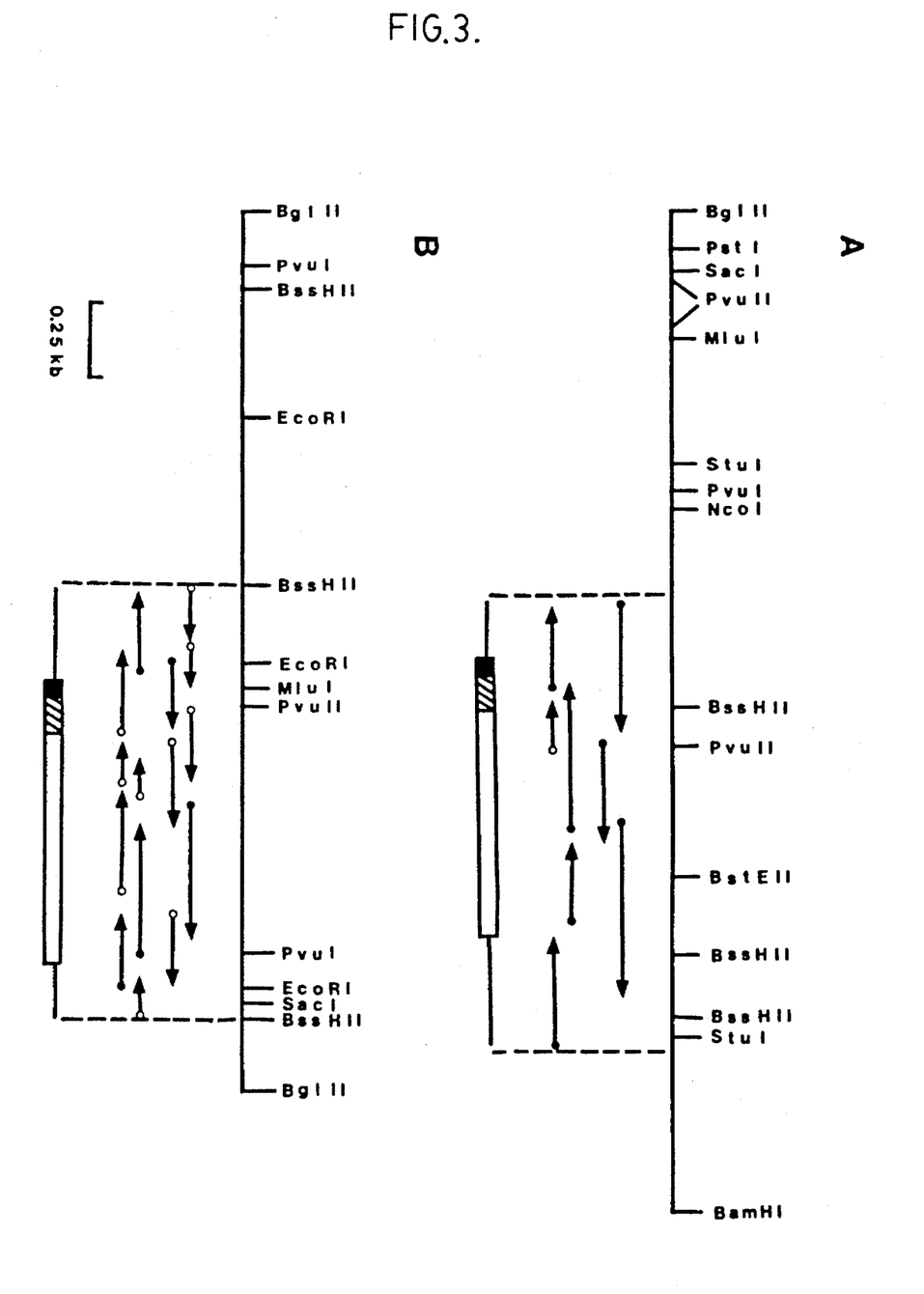
FIG. 3 illustrates restriction endonuclease maps and sequencing strategies in sequencing DNA fragments containing sprA and sprB.

In order to determine the nucleic acid sequence of the protease genes, the 3.2 kb BamHI–BglII fragment of sprA and the 2.8 kb BqlII fragment of sprB were subcloned into pUC18 to facilitate further structural characterization. As shown in FIG. 3, the restriction maps of these subclones and the strategies which were used to sequence the 1.4 kb SalI fragment containing sprA and the 1.4 kb BssHII fragment containing sprB are shown. The resultant DNA sequences of sprA and sprB are shown in FIGS. 4 and 5, respectively. The predicted amino acid sequence of protease A differed from the published sequence by the amidation of amino acid 133, whereas that of protease B was identical to the published sequence, (see Fujinaga. M., L. T. J. Delbaere, G. D. Brayer, and M. N. G. James (1985), *Refined Structure of α-lytic protease at 1.7 A resolution; Analysis of hyrodgen bonding and solvent structure*, J. Mol. Biol. 183:479–502).

Analyzing the sequences of FIGS. 4 and 5, it is apparent that each sequence contains a large open reading frame with the coding region of the mature protease situated at the 3' end. For the protease A and protease B genes, the sequence encoding the carboxy-terminus of the protease is followed immediately by a translation stop codon. At the other end of the sequence, the predicted amino acid sequences appear to extend beyond the amino-termini of the mature proteases A and B by an additional 116 amino acids for sprA of FIG. 4 and 114 amino acids for sprB of FIG. 5. The putative GTG initiation codons at each of these positions (–116 for FIG. 4; –114 for FIG. 5) are each preceded by a potential ribosome binding site (as indicated by the series of five dots above the sequence) and followed by a sequence which encodes a signal peptide. The processing site for the signal peptidase (identified by the light arrow in FIGS. 4 and 5) is predicted at 38 amino acids from the amino-terminus of the putative precursor. [For clarity, that part of the nucleic acid sequences of FIGS. 4 and 5 corresponding to the signal peptide portion of sprA and sprB is reproduced in FIGS. 4A and 5A, respectively]. The propeptide is encoded by the remaining sequence between the signal processing site (light arrow) and the start of the mature protein (indicated at the dark arrow). [For clarity, that part of nucleic acid sequences of FIGS. 4 and 5 corresponding to the propeptide portion of sprA and sprB is reproduced in FIGS. 4B and 5B, respectively]. The mature protease is encoded by the codon sequence 1 through 181 for FIG. 4 and 1 through 185 for FIG. 5. [For clarity, that part of the nucleic acid sequences of FIGS. 4 and 5 corresponding to the mature protein portion of sprA and sprB is reproduced in FIGS. 4C and 5C, respectively]. The amino acid sequence for codons –116 through +181 of FIG. 4 and the amino acid sequence for codons –114 through +185 of FIG. 5, when made in the living cell *S. griseus,* are acted upon in a manner to produce in the culture medium externally of the living cells the mature bioactive enzymes protease A and protease B. The processing involved in accordance with the contained information encoded by that portion of the gene from start of the promoter to start of the mature protein in each case included providing a secretory address, the correct signal peptide processing site, the necessary propeptide structure not only for secretion but also for correct disulphide bond formation concomitant with secretion, and competent secretion in bioactive form.

In accordance with this invention, the ability of the signal peptide to direct the secretion of bioactive protein was established by inserting known DNA sequences at the beginning and at the end of known sequences. For example, consider the sequence shown in FIG. 5. In particular, the promoter and initiator ATG of the aminoglycoside phosphotransferase gene, (Thompson, C. J., and G. S. Gray (1983), *Nucleotide sequence of a streptomycete aminoglycoside phosphotransferase gene and its relationship to phosphotransferases encoded by resistance plasmids,* Proc. Natl. Acad. Sci. USA, 80:5190–5194) had been inserted preceding the second codon (AGG at –113) of the signal sequence of FIG. 5. Due to the insertion of this new promoter and initiator, the sprB gene, now under the control of this non-native promoter, directed both elevated levels and earlier expression of proteolytic activity when compared with the unaltered sprB gene. The secretion of bioactive protease B in this construction indicated that nucleic acid sequences preceding the GTG initiation codon at –114 are not required for the correct secretion of the protease B in bioactive form, provided an active and competent promoter is placed in the precise location indicated.

In order further to demonstrate the universality of the discovered signal peptide, the SprB coding region was replaced with a gene sequence encoding the mature amylase from S. griseus. Hence the nucleic acid sequence encoding the amylase was inserted in place of the sequence of FIG. 5 to the right of the light arrow. It was determined that the resulting genetic construction directed the production of an extracellular protein having an N-terminal alanine, properly positioned intramolecular disulphide bonds, and exhibiting amylolytic activity at a level comparable to that of a similar construction with the natural signal peptide of amylase. In accordance with this invention, the 38 amino acid signal peptide of FIGS. 4 and 4A and 5 and 5A is sufficient to direct the secretion of non-native protein in bioactive form.

Figure 6A:
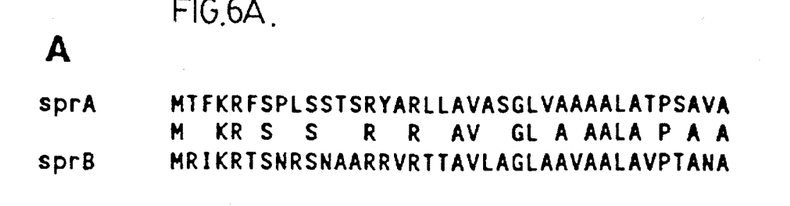
FIGS. 6A, 6B, and 6C show an alignment of the amino acid sequences deduced from sprA and sprB to develop homology between the two sequences.
Figure 6B:
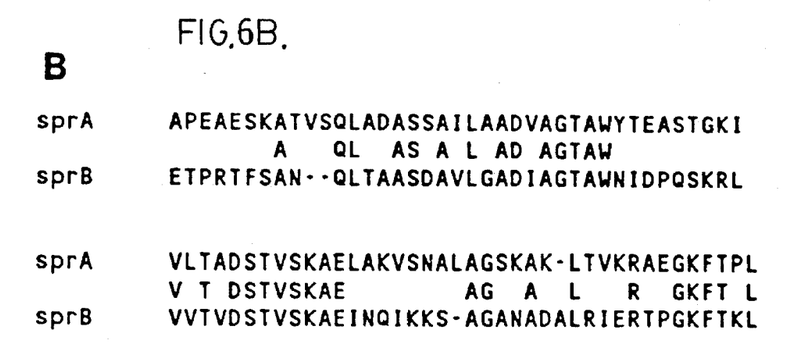
Figure 6C:
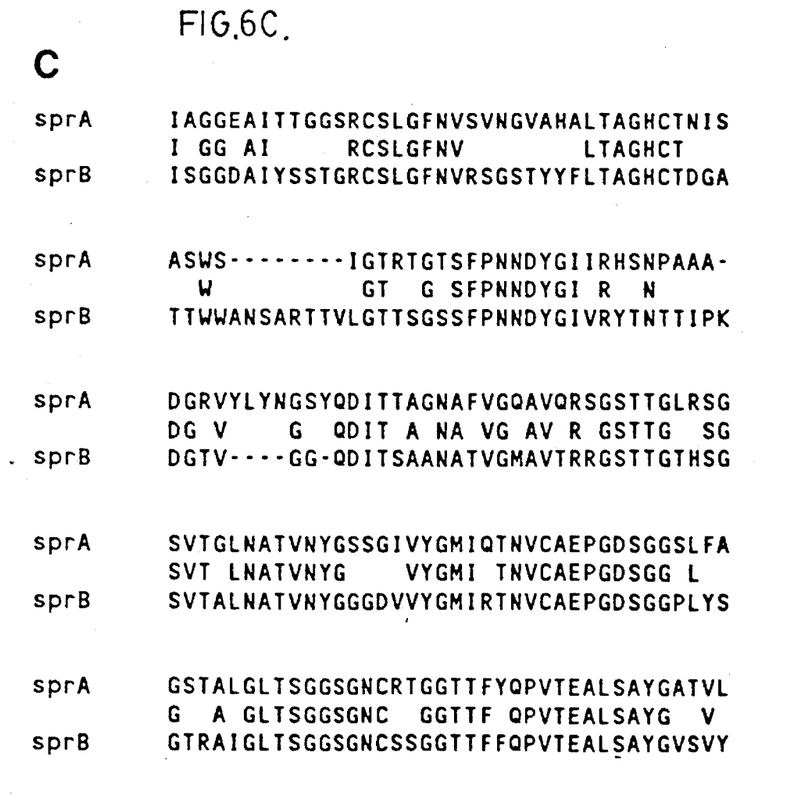

Since both signal sequences encode for the signal peptides of FIGS. 4 and 4A and 5 and 5A, the organization of the coding regions of sprA and sprB were investigated by comparing the amino acid homology of the encoded peptide sequences. Such comparisons are set out in FIG. 6 where amino acid homology has been compared for the signal peptide of FIG. 6a, the propeptide of FIG. 6b and the mature protease of FIG. 6c. A summary of such homology is provided in the following Table I.

TABLE I

Homology of sprA and sprB Coding Regions

|  | Length (codons) | Protein Homology % | DNA Homology % |
| --- | --- | --- | --- |
| Signal | 38 | 50 | 58 |
| Propeptide | 79 | 43 | 62 |
| NT protease[a] | 87 | 45 | 58 |
| CT protease[b] | 103 | 75 | 75 |
| Total Protease | 190 | 61 | 67 |
| Total coding region | 307 | 55 | 65 |

[a]amino-termini of mature proteases (amino acids 1–87)
[b]carboxy-termini of mature proteases (amino acids 88–190)

The alignment of amino acid sequences translated from the coding regions of the sprA and sprB genes indicates an overall homology of 54% on the basis of amino acid identity. As indicated in Table I, the sequence homology is not uniformly distributed throughout the coding region of the sprA and sprB genes. The carboxy-terminal domains of the proteases A and B are 75% homologous as noted under the heading "CT protease" whereas the average homology for the remainder of the coding region is only 45%, indicated under the heading "NT protease". The amino terminal domains containing the signal and propeptide regions were similar in both extent of homology and distribution of consensus sequences, as indicated under the headings "signal" and "propeptide". The unexpectedly high DNA sequence homology relative to that of the protein sequences is particularly due to the 61% conservation in the third position of each codon of the sequence. These investigations, revealing the close homology between sprA and sprB genes, suggest that both genes originated by duplication of a common ancestral gene. With appropriate care and investigation, the commonality of the signal peptides can be determined, thus establishing the cue for secretion of proteins and hence providing sufficient information to construct, from the signal DNA of sprA and sprB, a single nucleic acid sequence which will be competent to direct protein secretion.

In accordance with the invention, a recombinant DNA sequence can be developed which encodes for desired protein where the expressed protein, in conjunction with the signal peptide and optionally the propeptide, provide for secretion of the desired protein in bioactive form. The recombinant DNA sequence may be inserted in a suitable vector for transforming a desired cell for manufacturing the protein. Suitable expression vectors may include plasmids and viral phages. As is appreciated by those skilled in the art, the bioactivity of secretory proteins is assured by establishing the correct configuration of intramolecular disulphide bonds. Thus, suitable prokaryotic hosts may be selected for their ability to display enzymatic activity of a type typified by, but not limited to, that of protein disulphide oxidoreductase, EC 5.3.4.1.

The particular protein encoded by the recombinant DNA sequence may include eukaryotic secretory enzymes, such as prochymosin, chymotrypsin, trypsins, amylases, lignineases, chymosin, elastases, lipases, and cellulases; prokaryotic secretory enzymes such as glucose, isomerase, amylases, lipases, pectinases, cellulases, proteinases, oxidases, lignases; blood factors, such as Factor VIII and Factor IX and Factor VIII-related biosynthetic blood coagulant proteins; tissue-type plasminogen activator; hormones, such as proinsulin; lymphokines, such as beta and gamma-interferon, and interleukin-2; enzyme inhibitors, such as extracellular proteins whose action is to destroy antibiotics either enzymatically or by binding, for example, a B-lactamase inhibitor, a-trypsin inhibitor; growth factors, such as organism or nerve growth factors, epidermal growth factors, tumor necrosis factors, colony stimulating factors; immunoglobulin-related molecules, such as synthetic, designed, or engineered antibody molecules; cell receptors, such as cholesterol receptor; viral molecules, such as viral hemaglutinins, AIDS antigen and immunogen, hepatitis B antigen and immunogen, foot-and-mouth disease virus antigen and immunogen; bacterial surface effectors, such as protein A; toxins such as protein insecticides, algicides, fungicides, and biocides; and systemic proteins of medical importance, such as myocardial infarct protein (MIP), weight control factor (WCF), calloric rate protein (CRP) and hirutin (HRD).

One skilled in the art can easily determine whether the use of any known or unknown organism will be within the scope of this invention in accordance with the above discussion and the following examples.

Microorganisms which may be useful in this respect as potential prokaryotic expression hosts include: Order: Actinomycetales; Family: Actinomycetaceae Genus: Matruchonema, Lactophera; Family Actinobacteria: Genus Actinomyces, Agromyces, Arachina, Arcanobacterium, Arthrobacter, Brevibacterium, Cellulomonas, Curtobacterium, Microbacterium, Oerskovia, Promicromonospora, Renibacterium, Rothia; Family Actinoplanetes: Genus Actinoplanes, Dactylosporangium, Micromonospora; Family *Nocardioform actinomycetes:* Genus Caseobacter, Corynebacterium, Mycobacterium, Nocardia, Rhodococcus; Family Streptomycetes: Genus Streptomyces, Streptoverticillium; Family Maduromycetes: Genus Actinomadura, Excellospora, Microspora, Planospora, Spirillospora, Streptosporangium; Family Thermospora: Genus Actinosynnema, Nocardiopsis, Thermophilla; Family Microspora: Genus Actinospora, Saccharospora; Family Thermoactinomycetes: Genus Thermoactinomyces; and the other prokaryotic genera: Acetivibrio, Acetobacter, Achromobacter, Acinetobacter, Aeromonas, Bacterionema, Bifidobacterium, Flavobacterium, Kurthia, Lactobacillus, Leuconostoc, Myxobacteria, Propionibacterium.

The following species from the genus Streptomyces are identified as particularly suitable as hosts: *acidophillus, albus, amylolyticus, argentiolus, aureofaciens, aureus, candidus, cellostaticus, cellulolyticus, coelicolor, creamorus, diastaticus, farinosus, flaveolus, flavogriseus, fradiae, fulvoviridis, fungicidicus, gelaticus, glaucescens, globisporus, griseolus, griseus, hygroscopicus, ligninolyticus, lipolyticus, lividans, moderatus, olivochromogenus, parvus, phaeochromogenes, plicatus, proteolyticus, rectus, roseolus, roseoviolaceus, scabies, thermolyticus, tumorstaticus, venezuelae, violaceus, violaceus-ruber, violascens,* and *viridochromogenes.*

| | |
|---|---|
| *acrimycini* | *fendae* |
| *alboniger* | *griseofuscus* |
| *ambofaciens* | *kanamyceticus* |
| *antibioticus* | *kasugaensis* |
| *aspergilloides* | *koganeiensis* |
| *chartreusis* | *lavendulae* |
| *clavuligerus* | *parvulus* |
| *diastatochromogenes* | *peucetius* |
| *echinatus* | *reticuli* |
| *erythraeus* | *rimosus* |
| | *vinaceus* |

Also, the following eukaryotic hosts are potentially useful in the practice of this invention:

Absidia, Acremonium, Acrophialophora, Acrospeira, Alternaria, Arthrobotrys, Ascotricha, Aureobasidium, Beauveria, Bispora, Bjerkandera, Calocera, Candida, Cephaliophora, Cephalosporium, Cerinomyces, Chaetomium, Chrysosporium, Circinella, Cladosporium, Cliomastix, Coccospora, Cochliobolus, Cunninghamella, Curvularia, Custingophara, Dacrymyces, Dacryopinax, Dendryphion, Dictosporium, Doratomyces, Drechslera, Eupenicillium, Flammulina, Fusarium, Gliocladium, Gliomnastix, Graphium, Hansenula, Humicola, Hyalodendron, Isaria, Kloeckera, Kluyveromyces, Lipomyces, Mammaria, Merulius, Microascus, Monodictys, Monosporium, Morchella, Mortierella, Mucor, Myceliophthora, Mycrothecium, Neurospora, Oedocephalum, Oidiodendron, Pachysolen, Papularia, Papulaspora, Penicillium, Peniophora, Periconia, Phaeocoriolellus, Phanerochaete, Phialophora, Piptocephalis, Pleurotus, Preussia, Pycnoporus, Rhioncladiella, Rhizomucor, Rhizopus, Rhodotorula, Robillarda, Saccharomyces, Schwanniomyces, Scolecabasidium, Scopulariopsis, Scytalidium, Stachybotrys, Tetracluium, Thamnidium, Thermioascus, Thermomyces, Thiclavia, Tolypocladium, Torula, Torulopsis, Trametes, Tricellula, Trichocladium, Trichoderma, Trichurus, Truncatella, Ulocladium, Ustilago, Verricullium, Wardomyces, Xylogone, Yarrowia.

Preferred embodiments of the invention are exemplified in the following procedures. Such procedures and results are by way of example and are not intended to be in any way limited to the scope of the claims.

PREPARATIONS

Strains and Plasmids

*Streptomyces griseus* (ATCC 15395) was obtained from the American Type Culture Collection. *Streptomyces lividans* 66 (Bibb, M. J., J. L. Schottel, and S. N. Cohen (1980), *A DNA cloning system for interspecies gene transfer in antibiotic-producing Stretomyces,* Nature 284:526–531) and the plasmids pIJ61 and pIJ702 from the John Innes Institute; Thompson, C. J., T. Kieser, J. M. Ward, and D. A. Hopwood (1982), *Physical analysis of antibiotic-resistance genes from Streptomyces and their use in vector construction,* Gene 20:51–62; Katz, E., C. J. Thompson, and D. A. Hopwood (1983), *Cloning and expression of the tyrosinase gene from Streptomyces antibioticus in Streptomyces lividans,* J. Gen. Microbiol., 129:2703–2714). *E. coli* strain HB101 (ATCC 33694) was used for all transformations. Plasmids pUC8, pUC18 and pUC19 were purchased from Bethesda Research Laboratories.

Media, Growth and Transformation

Growth of Streptomyces mycelium for the isolation of DNA or the preparation of protoplasts was as described in Hopwood, D. A., M. J. Bibb, K. F. Chater, T. Kieser, C. J. Bruton, H. M. Kieser, D. J. Lydiate, C. P. Smith, J. M. Ward, and H. Schrempf (1985), *Genetic Manipulation of Streptomyces, A Laboratory Manual,* The John Innes Foundation, Norwich, UK. Protoplasts of *S. lividans* were prepared by lysozyme treatment, transformed with plasmid DNA, and selected for resistance to thiostrepton, as described in Hopwood, D. A., M. J. Bibb, K. F. Chater, T. Kieser, C. J. Bruton, H. M. Kieser, D. J. Lydiate, C. P. Smith, J. M. Ward, and H. Schrempf (1985), *Genetic Manipulation of Streptomyces, A Laboratory Manual,* The John Innes Foundation, Norwich, UK. Transformants were screened for proteolytic or amylolytic activity on LB plates containing 30 ug/ml thiostrepton, and either 1% skim milk or 1% corn starch, respectively. *E. coli* transformants were grown on YT medium containing 50 ug/ml ampicillin.

Materials

Oligonucleotides were synthesized using an Applied Biosystem 380A DNA synthesizer. Columns, phosphoramidites, and reagents used for oligonucleotide synthesis were obtained from Applied Biosystems, Inc. through Technical Marketing Associates. Oligonucleotides were purified by polyacrylamide gel electrophoresis followed by DEAE cellulose chromatography. Enzymes for digesting and modifying DNA were purchased from New England Biolabs, and used according to the supplier's recommendations. Radioisotopes [$\alpha$-32P]dATP (3000 Ci/mmol) and [$\alpha$-32P] ATP (~3000 Ci/mmol) were from Amersham. Thiostrepton was donated by Squibb.

EXAMPLE 1—Isolation of DNA

Chromosomal DNA was isolated from Streptomyces as described in Chater, K. F., D. A. Hopwood, T. Kieser, and C. J. Thomson (1982), *Gene cloning in Streptomyces,* Curr. Topics Microbiol. Immunol., 96:69–95, except that sodium dodecyl sarcosinate (final conc. 0.5%) was substituted for sodium dodecyl sulfate. Plasmid DNA of transformed *S. lividans* was prepared by an alkaline lysis procedure as set out in Hopwood, D. A., M. J. Bibb, K. F. Chater, T. Kieser, C. J. Bruton, H. M. Kieser, D. J. Lydiate, C. P. Smith, J. M. Ward, and H. Schrempf (1985), *Genetic Manipulation of Streptomyces, A Laboratory Manual,* The John Innes Foundation, Norwich, UK. Plasmid DNA from *E. coli* was purified by a rapid boiling method (Holmes, D. S., and M. Quigley (1981). *A rapid boiling method for the preparation of bacterial plasmids,* Anal. Biochem., 114:193–197). DNA fragments and vectors used for all constructions were separated by electrophoresis on low melting point agarose, and purified from the molten agarose by phenol extraction.

EXAMPLE 2—Construction of Genomic Library

Chromosomal DNA of *S. griseus* ATCC 15395 was digested to completion of BamHI and fractionated by electrophoresis on a 0.8% low melting point agarose gel. DNA fragments ranging in size from 4 to 12 kilobase pairs (kb) were isolated from the agarose gel. The plasmid vectors pUC18 and pUC19 were digested with BamHI, and treated with calf intestinal alkaline phosphatase (Boehringer Mannheim). The *S. griseus* BamHI fragments (0.3 ug) and vectors (0.8 ug) were ligated in a final volume of 20 ul as described in Maniatis, T., E. F. Fritsch, and J. Sambrook (1982), *Molecular Cloning, A Laboratory Manual*, Cold Spring Harbor Laboratory, Cold Spring Harbor, N.Y.). Approximately 8000 transformants of HB101 were obtained from each ligation reaction.

EXAMPLE 3—Subcloning of Protease Gene Fragments

A hybrid Streptomyces-*E. coli* vector was constructed by ligating pIJ702, which had been linearized by BamHI, into the BamHI site of pUC8. The unique BglII site of this vector was used for subcloning BamHI and BglII fragments of the protease genes. Other fragments were adapted with BamHI linkers to facilitate ligation into the BglII site. The hybrid vector, with pUC8 inserted at the BamHI site of pIJ702, was incapable of replicating Streptomyces. However, the *E. coli* plasmid could be readily removed prior to transforming *S. lividans* by digestion with BamHI followed by recircularization with T4 ligase.

EXAMPLE 4—Construction for Testing the sprB Signal Peptide

The 0.4 kb Sau3AI-NcoI fragment containing the aminoglycoside phosphotransferase gene promoter was isolated from pIJ61 and subcloned into the BamHI and NcoI sites of a suitable vector. The NcoI site containing the initiator ATG was joined to the MluI site of the sprB signal using two 43-mer oligonucleotides, which reconstructed the amino-terminus of the signal peptide. An amylase gene of *S. griseus* was adapted by ligating a 14-mer PstI linker to a SmaI site in the third codon. This removed the signal peptide and restored the amino-terminus of the mature amylase. The HaeII site of the sprB signal was joined to the PstI site of the amylase subclone using two 26-mer oligonucleotides, which reconstructed the carboxy-terminus of the signal peptide.

EXAMPLE 5—Hybridization

A 20-mer (5'TTCCC(C/G)AACAACGACTACGG3') oligonucleotide was designed from an amino acid sequence (FPNNDYG) which was common to both proteases. For use as a hybridization probe, the oligonucleotide was end-labelled using T4 polynucleotide kinase (New England Biolabs) and [α-32P]ATP. Digested genomic or plasmid DNA was transferred to a Hybond-N nylon membrane (Amersham) by electroblotting and hybridized in the presence of formamide (50%) as described in Hopwood, D. A., M. J. Bibb, K. F. Chater, T. Kieser, C. J. Bruton, H. M. Kieser, D. J. Lydiate, C. P. Smith, J. M. Ward, and H. Schrempf (1985), *Genetic Manipulation of Streptomyces, A Laboratory Manual*, The John Innes Foundation, Norwich, UK. The filters were hybridized with the labelled oligonucleotide probe at 30° C. for 18 h, and washed at 47° C. The *S. griseus* genomic library was screened by colony hybridization as described in Wallace, R. B., M. J. Johnson. T. Hirose, T. Miyake, E. H. Kawashima, and K. Itakura (1981), *The use of synthetic oligonucleotides as hybridization probes, II. Hybridization of oligonucleotides of mixed sequence to rabbit globin DNA*, Nucl. Acids Res, 9:879–894.

EXAMPLE 6—DNA Sequencing

The sequences of sprA and sprB were determined using a combination of the chemical cleavage sequencing method (Maxam, A., and W. Gilbert (1977), *A new method for sequencing DNA*, Proc. Natl. Acad. Sci. U.S.A., 74:560–564) and the dideoxy sequencing method (Sanger, F., S. Nicklen, and A. R. Coulson (1977), *DNA sequencing with chain terminating inhibitors*, Proc. Natl. Acad. Sci. U.S.A., 74:5463:5467). Restriction fragments were end-labeled using either polynucleotide kinase or the large fragment of DNA Polymerase I (Amersham), with the appropriate radiolabeled nucleoside triphosphate. Labeled fragments were either digested with a second restriction endonuclease or strand-separated, followed by electroelution from a polyacrylamide gel. Subclones were prepared in the M13 bacteriophage and the dideoxy sequencing reactions were run using the −20 universal primer (New England Biolabs). In some areas of strong secondary structure, compressions and polymerase failure necessitated the use of either inosine (Mills, D. R., and F. R. Kramer (1979), *Structure independent nucleotide sequence analysis*, Proc. Natl. Acad. Sci. U.S.A., 76:2232–2235) or 7-deazaguanosine (Mizusana, S., S. Nishimura, and F. Seela (1986), *Improvement of the dideoxy chain termination method of DNA sequencing by use of deoxy-7-deazoquanosine triposphate in place of dGTP*, Nucleic Acids Res., 14:1319–1324) analogs in the dideoxy reactions to clarify the sequence. The sequence were compiled using the software of DNASTAR™ (Doggette, P. E., and F. R. Blattner (1986), *Personal access of sequence databases on personal computers*, Nucleic Acids Res., 14:611–619).

Although preferred embodiments of the invention have been described in detail, it will be understood by those skilled in the art that variations may be made thereto without departing from either the spirit of the invention or the scope of the appended claims.

What is claimed is:

1. A gene expression system for secretion of bioactive disulfide bond-containing proteins from a host of the genus Streptomyces, wherein:

said expression system comprises a promoter sequence that is operably linked to a nucleotide sequence encoding a polypeptide;

said polypeptide comprises the signal peptide of *Streptomyces griseus* protease B and a heterologous protein that is operably linked to said signal peptide;

said heterologous protein is a disulfide bond-containing protein; and said signal peptide, when said gene expression system is expressed in a host of the genus Streptomyces, directs secretion of said heterologous protein in its bioactive disulfide bond-containing form.

2. A gene expression system according to claim 1, wherein said signal peptide comprises the amino acid sequence MRIKRTSNRSNAARRVRTTAVLAG-LAAVAALAVPTANA.

3. A gene expression system according to claim 1 wherein said heterologous protein is a colony stimulating factor.

* * * * *